(12) United States Patent
Grijpma et al.

(10) Patent No.: US 7,572,838 B2
(45) Date of Patent: Aug. 11, 2009

(54) METHOD FOR PROVIDING SHAPED BIODEGRADABLE AND ELASTOMERIC STRUCTURES OF (CO) POLYMERS OF 1,3-TRIMETHYLENE CARBONATE (TMC), SHAPED BIODEGRADABLE AND ELASTOMERIC STRUCTURES, AND THE USE OF THESE STRUCTURES

(75) Inventors: Dirk Wybe Grijpma, Hengelo (NL); Ana Paula Gomes Moreira Pêgo, Enschede (NL); Jan Feijen, Hengelo (NL)

(73) Assignee: Universiteit Twente, NB Enschede (NL)

( * ) Notice: Subject to any disclaimer, the term of this patent is extended or adjusted under 35 U.S.C. 154(b) by 54 days.

(21) Appl. No.: 10/533,941

(22) PCT Filed: Nov. 5, 2003

(86) PCT No.: PCT/EP03/12425

§ 371 (c)(1),
(2), (4) Date: Oct. 25, 2005

(87) PCT Pub. No.: WO2004/041318

PCT Pub. Date: May 21, 2005

(65) Prior Publication Data

US 2006/0241201 A1    Oct. 26, 2006

(30) Foreign Application Priority Data

Nov. 5, 2002    (NL) .................................... 1021843

(51) Int. Cl.
*C08F 2/46* (2006.01)

(52) U.S. Cl. .................... 522/154; 522/150; 522/84; 522/86; 522/85; 522/153; 264/446; 264/448; 264/488; 264/494; 252/182.12; 252/182.13; 252/182.11; 428/411.1; 428/412

(58) Field of Classification Search ................ 522/85, 522/86, 84, 150, 153, 154; 428/411.1, 412; 264/446, 448, 488, 494; 252/182.11, 182.12, 252/182.13

See application file for complete search history.

(56) References Cited

U.S. PATENT DOCUMENTS

| | | | | |
|---|---|---|---|---|
| 4,496,446 A | * | 1/1985 | Ritter et al. ................. 522/162 |
| 5,889,075 A | * | 3/1999 | Roby et al. ................... 522/87 |
| 6,093,792 A | * | 7/2000 | Gross et al. ................. 528/354 |
| 6,887,974 B2 | * | 5/2005 | Pathak ........................ 530/200 |
| 6,984,393 B2 | * | 1/2006 | Amsden ..................... 424/423 |
| 7,057,019 B2 | * | 6/2006 | Pathak ........................ 530/362 |
| 7,211,651 B2 | * | 5/2007 | Pathak ........................ 530/382 |
| 2002/0114775 A1 | * | 8/2002 | Pathak ..................... 424/78.17 |
| 2003/0077272 A1 | * | 4/2003 | Pathak ..................... 424/94.64 |
| 2003/0105245 A1 | * | 6/2003 | Amsden ..................... 525/450 |
| 2003/0232929 A1 | * | 12/2003 | Huang et al. ................ 525/412 |

FOREIGN PATENT DOCUMENTS

DK    DE 196 08 250 A    10/1987

OTHER PUBLICATIONS

Pego et al. Enhanced mechanical properties of 1,3-trimethylene carbonate polymers and networks Polymer, vol. 44, Issue 21, Oct. 2003, pp. 6495-6504.*
Zhu et al. Synthesis, Properties, and Biodegradation of Poly(1,3-Trimehylene carbonate). Macromoleculaes 1991, 24, 1736-1740.*
Wang et al. Synthesis and Characterization of ABA-Type block copolymers of Poly(tirmethylene carbonate) with Poly(ethylene gylcol): Bioerodible copolymer. Journal f POlymer Science: Part A: Polymer Chemistry, vol. 36, 695-702 (1998).*
M. Schappacher et al. Study of trimthylene carbonate-co-e-caprolactone polymer—Part 1: Preparation of a new nerve guide through controlled random copolymerization using rare earth elements. Biomaterials 22 (2001) 2849-2855.*
AutoClave definition from Dictonary.com [retrived online Dec. 19, 2008]. retrieved from <URL:http://dictionary/reference.com/browse/autoclave>.*
International Search Report dated Mar. 22, 2004 Form PCT/ISA/210.

* cited by examiner

*Primary Examiner*—Sanza L McClendon
(74) *Attorney, Agent, or Firm*—Harness, Dickey & Pierce, P.L.C.

(57) ABSTRACT

The present invention relates to methods for providing shaped biodegradable and elastomeric structures of (co)polymers of 1,3trimethylene carbonate (TMC) with improved (mechanical) properties which can be used for tissue or tissue component support, generation or regeneration. Such shaped biodegradable elastomeric structures are obtainable by forming homopolymers and/or copolymers of 1,3-trimethylene carbonate (TMC) into a desired shape and irradiating said desired shape with actinic radiation in an inert atmosphere.

21 Claims, 2 Drawing Sheets

Figure 1:
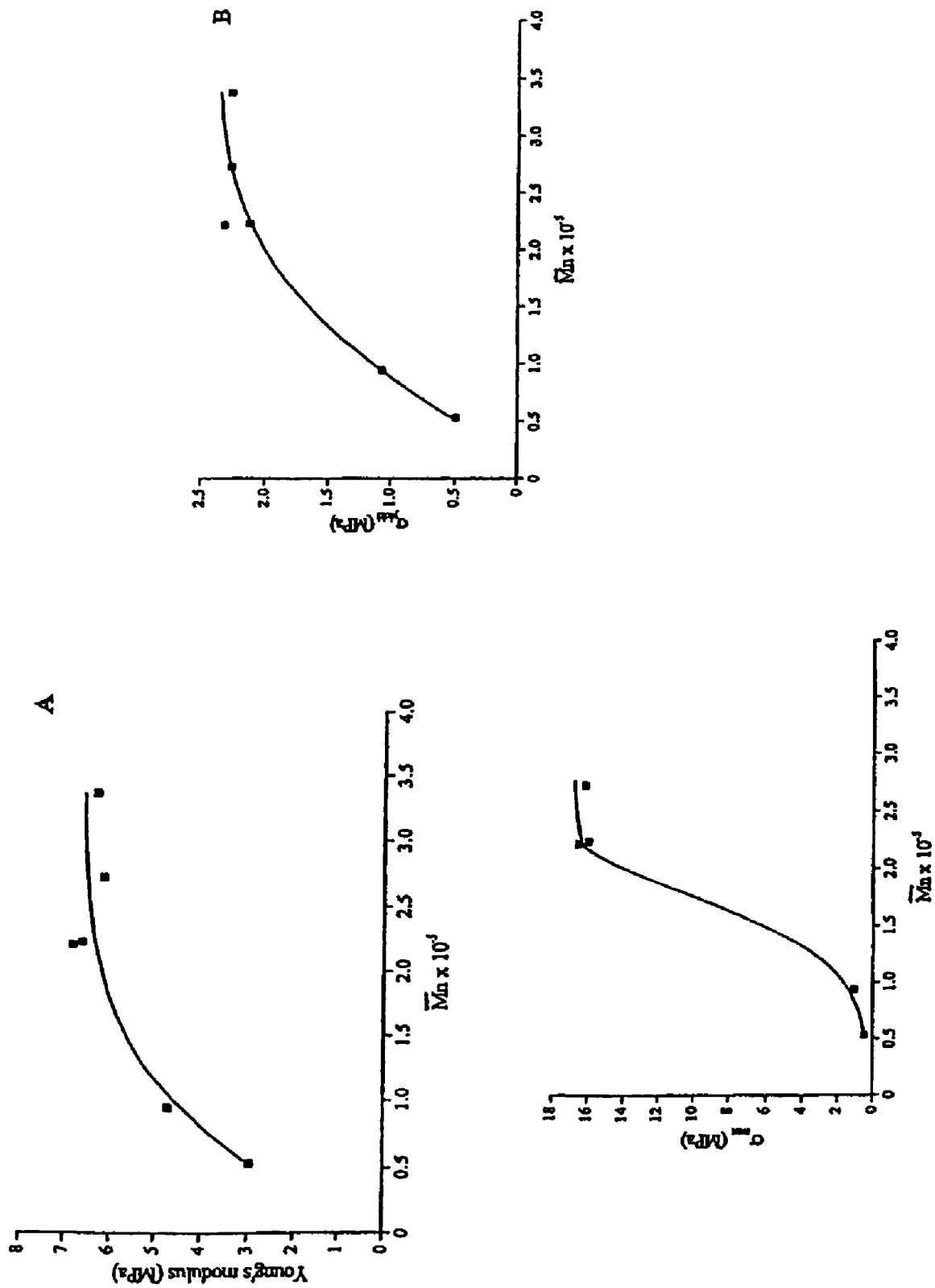

METHOD FOR PROVIDING SHAPED BIODEGRADABLE AND ELASTOMERIC STRUCTURES OF (CO) POLYMERS OF 1,3-TRIMETHYLENE CARBONATE (TMC), SHAPED BIODEGRADABLE AND ELASTOMERIC STRUCTURES, AND THE USE OF THESE STRUCTURES

The present invention relates to methods for providing shaped biodegradable and elastomeric structures of (co)polymers of 1,3-trimethylene carbonate (TMC) with improved (mechanical) properties. The present invention further relates to shaped biodegradable elastomeric structures obtainable by said methods, the use of said shaped biodegradable and elastomeric structures in or as implants, matrices, and/or support devices, and implants, matrices and/or support devices comprising said shaped biodegradable and elastomeric structures.

The need for biodegradable and elastomeric structures for the preparation of implants, matrices, and/or support devices, which can be used for tissue support, tissue generation or tissue regeneration, has been well documented in the literature in recent years.

For tissue generation or regeneration the properties of biodegradable and elastomeric structures, like gels or porous or solid scaffolds, on or in which seeded cells can organize and develop into a desired tissue in vitro and/or in vivo, would ideally resemble the properties of the extracellular matrix (ECM). Such biodegradable and elastomeric structures withstand the dynamics of the body or tissue culture and in addition provide adequate micro-stresses to the cells as well as ensure (mechanical) stability and structural integrity to the developing tissue or tissue component.

The often used glycolide and lactide based (co)polymers are not well suited for the preparation of these biodegradable and elastomeric structures since these structures are rigid as their glass transition temperature ($T_g$) is above body temperature. Examples of structures that have previously been investigated include structures of (co)polymers of lactide (LA) and ε-caprolactone (CL), and poly-4-hydroxybutyrate and poly (glycerol-sebacate).

1,3-trimethylene carbonate (TMC), an aliphatic carbonate, has long been known and its suitability for the preparation of biodegradable and elastomeric structures has been previously evaluated. Structures comprising (co)polymers of 1,3-trimethylene carbonate (TMC) have a very low modulus and low tensile strength and these poor (mechanical) properties discouraged any practical application as a biodegradable elastomeric structure.

Pêgo et al. (2001), "Copolymers of trimethylene carbonate and ε-caprolactone for porous nerve guides: synthesis and properties", *J. Biomater. Sci. Polym. Ed.* 12, pp 35-53, disclose that structures comprising very high molecular weight 1,3-trimethylene carbonate (TMC) ($\overline{M}_n$=290,000 and $\overline{M}_w$=552,000) exhibit improved (mechanical) properties probably due to strain-induced crystallization ($T_m$=36° C.).

This self-reinforcement, also observed for natural rubber, can be the origin of the observed improved tensile strength and extensibility of these strain-crystallizable structures. In addition, structures comprising high molecular weight 1,3-trimethylene carbonate (TMC) were totally resorbed after 3 weeks of subcutaneous implantation in rats. The degradation and resorption of the polymer induced only a mild tissue reaction.

However, the biodegradable structures comprising 1,3-trimethylene carbonate (TMC) according to Pêgo et al. still do not provide a biodegradable elastomeric structure for optimal tissue support, tissue generation and tissue regeneration, especially with respect to dynamic and/or static loading for a long period without substantial permanent deformation, the possibility of simple and repeated sterilization, and flexibility regarding the possibility to vary the (mechanical) properties depending on the desired application. The term "no substantial permanent deformation" as used herein is understood to mean a permanent deformation of less than 10% of the applied elongation.

Therefore, the need still remains for a shaped biodegradable and elastomeric structure which optimally withstands the dynamics of the body or tissue culture and which optimally provides adequate micro-stresses to the cells as well as (mechanical) stability and structural integrity to the developing tissue or tissue component.

According to the present invention, the above need is fulfilled with a method providing a shaped biodegradable and elastomeric structure comprising forming homopolymers and/or copolymers of 1,3-trimethylene carbonate (TMC) into a desired shape and irradiating said desired shape with actinic radiation in an inert atmosphere The inventors surprisingly found that irradiation in an inert atmosphere of formed homopolymers and/or copolymers of 1,3-trimethylene carbonate (TMC)) resulted in an improvement of the (mechanical) properties of the provided structure as compared to the structures as disclosed by Pêgo et al. Due to these improvements, the shaped biodegradable elastomeric structures according to the invention are highly suitable for use in or as implant, matrix, and/or support device both in vivo and in vitro.

This was surprising because it was generally assumed that irradiation of 1,3-trimethylene carbonate (TMC) (co)polymers predominantly results in chain-scissioning causing a deterioration instead of an improvement of the desired (mechanical) properties of the shaped biodegradable structure.

According to the present invention, the homopolymers and/or copolymers of 1,3-trimethylene carbonate (TMC) are formed into a desired shape. Any forming technique known in the art can be used for providing the desired shape such as injection molding, injection, extrusion, pressure molding, "in mold labeling", solvent casting, casting, freeze-drying or lithography.

The use of actinic radiation to obtain the shaped biodegradable elastomeric structure according to the present invention provides the formation of crosslinkages between the 1,3-trimethylene carbonate (TMC) (co)polymer chains resulting in a structure with improved (mechanical) properties.

In addition, the use of actinic radiation for the formation of crosslinkages between the 1,3-trimethylene carbonate (TMC) (co)polymer chains makes the use of often toxic compounds, which are generally used in chemical crosslinking, redundant. This is especially advantageous in case the shaped biodegradable elastomeric structure according to the invention is used for medical applications and/or cell culture. Furthermore, these often toxic compounds, and/or residues of these often toxic compounds, can have a negative effect on the properties of the end-product.

Because the irradiation dose can carefully, precisely, and reproducibly be controlled, the degree of crosslinking can also carefully, precisely and reproducibly be controlled. This results in a reproducible quality of the shaped biodegradable elastomeric structures according to the invention. Furthermore, by varying the radiation doses, a flexibility can be achieved with respect to preparing shaped biodegradable and elastomeric structures with desired properties.

In a preferred embodiment of the present invention, the provided (co)polymer has a number average molecular weight ($\overline{M}_n$) greater than 10,000. The use of (co)polymers of 1,3-trimethylene carbonate (TMC)) with an $\overline{M}_n$ lower than 10,000 have the drawback that the polymer is not sufficiently form-retaining, making the forming of a permanent structure more difficult. In addition, the (co)polymers with a number average molecular weight of 10,000 to 300,000, like 10,000, 20,000, 30,000, 40,000, 50,000, 75,000, 100,000, 135,000, 189,000, 200,000, 225,000, 250,000, 270,000 or 300,000, provide the additional advantage that they can easily be shaped into a desired form using standard techniques in contrast to (co)polymers with a higher molecular weight. Particularly suitable are the polymers with a number average molecular weight of 50,000 to 200,000 like 50,000, 60,000, 70,000, 80,000, 90,000, 100,000, 135,000, 150,000, 189,000, or 200,000, and in addition 135,000 to 189,000 or to 200,000.

According to the present invention, the actinic radiation provides crosslinkages between the (co)polymers while chain-scissioning is absent or within acceptable levels. Copolymers of 1,3-trimethylene carbonate (TMC), which are especially suitable to be crosslinked in combination with actinic radiation, are 1,3-trimethylene carbonate (TMC) (co)polymers with lactones (cyclic esters), cyclic carbonates, cyclic ethers, cyclic anhydrides, or cyclic depsipeptides (morpholine 2,5-dione derivatives).

These copolymers of 1,3-trimethylene carbonate (TMC) are preferably in the form of a statistical copolymer, a random copolymer, an alternating copolymer, a block polymer, a diblock copolymer, a triblock copolymer, a multiblock copolymer, a star-shaped block copolymer, and a graft block copolymer.

Examples of such copolymers are 1,3-trimethylene carbonate (TMC) (co)polymers with polyethylene oxide (PEO), polyethylene glycol (PEG) or ϵ-caprolactone (CL) like 1,3-trimethylene carbonate (TMC) (co)polymers with δ-valerolacton, 1,5-dioxepane-2-one, and ϵ-caprolactone, preferably poly(1,3,-trimethylene carbonate-co-ϵ-caprolactone) (poly(TMC-CL)).

The actinic radiation used is preferably a form of radiation that provides efficient crosslinking and none or little chain-scissioning together with a sufficiently high energy content. Examples of such actinic radiation are gamma-radiation, high-energy UV-radiation and electron radiation.

Actinic radiation with a high energy content has the advantage that the crosslinking process progresses relatively quickly, this being of particular importance with respect to production costs. Gamma radiation is especially suitable as high energy actinic radiation. Gamma radiation is an inexpensive, generally available radiation source which is easy and safe to use. The use of gamma radiation has the additional advantage that the (co)polymer structures are simultaneously crosslinked and sterilized, which is a prerequisite for the use of the shaped biodegradable elastomeric structures according to the invention for medical applications and cell culture.

In a preferred embodiment of the present invention, the radiation source is gamma radiation and the irradiation dosage is 5-100, like 5, 10, 25, 45 50, 65, 75, 80 or 100 kGy. The irradiation dosage in the range of 5-100 kGy, preferably 10-45, such as 10, 15, 20, 25, 30, 35, 40, or 45, kGy, results in effective crosslinking of the structure. At lower irradiation dosages the crosslinking process progresses disadvantageously slow. Similarly, at higher irradiation dosages the crosslinking process progresses disadvantageously fast. Further, the process can also become difficult to control in the latter case.

Specially recommended is an irradiation dosage of 10, 15, 25, 40 or 45 kGy. Such a dosage is easily obtained by making use of generally available radiation sources during a relatively short period of time. In particular, use can be made of existing medical sterilization equipment.

According to an embodiment of the present invention, the inert atmosphere is provided by means of a reduced pressure of less than $10^4$ Pa. Such a pressure can be readily obtained by making use of simple means such as for instance a membrane pump or a water jet pump.

According to another embodiment of the present invention, the inert atmosphere is provided by making use of an inert gas. Such gases are easy to handle and do not generally require any specially adapted production facilities such as for instance an explosion and flame proof chamber. The use of nitrogen is recommended as inert gas. Such a gas is inexpensive and generally available.

The shaped biodegradable elastomeric structures according to the present invention preferably are characterized by a creep rate of less than about 10% of the yield stress. For 1,3-trimethylene carbonate (TMC) this is approximately 0.2 MPa for poly(TMC). The creep rate of a structure is defined as a progressive deformation of the polymer material in the course of time while the structure is continually exposed to dynamic and/or static forces. Structures with the above creep rates are sufficiently able to withstand, both in vivo and in vitro, the dynamic and static forces occurring in the body and during tissue culture.

In addition, the shaped biodegradable elastomeric structures according to the present invention preferably are characterized by a degree of swelling of less than 400% in chloroform. Further, optimal results are achieved when the shaped biodegradable elastomeric structure according to the invention has a gel fraction of more than 10% by weight.

The above-described method provides shaped biodegradable and elastomeric structures which are resistant to the conditions which occur during sterilization, particularly in a generally available autoclave. This has the advantage that, if necessary, the end product can be sterilized just before the intended application such as implantation or tissue culture, which greatly simplifies pretreatment procedures like wash steps, incubation steps, purification steps, handling steps, transportation steps, etc.

As already outlined above, the method according to the invention provides a shaped biodegradable structure with excellent (mechanical) properties. Therefore, the present invention also relates to a shaped biodegradable structure obtainable by the above-described method.

The shaped biodegradable elastomeric structure according to the present invention is highly suitable for use as implants, matrices and support structures owing to the greatly improved (mechanical) properties like resistance to the dynamic and static loads both in the body and in the tissue culture, the absence of toxic substances, the biodegradability, the fact that they can be sterilized, and their suitable structure for cell growth.

The shaped biodegradable elastomeric structures according to the invention can be applied in biomedical practice. They can be used as implants that have a temporary function as a scaffold material for cells and cell growth or as a substitute material, for instance a heart valve or a separating membrane.

The structures can also be used as a matrix. This matrix is in general used in vitro to culture tissues and tissue components. The matrix can have a gel or porous structure, for instance for the culture of cells within the structure or be a solid structure, for instance for culture of cells on the surface in accordance with the desired application. Because the structures according to the invention are suitable for any application wherein it is necessary to provide a framework, scaffold and/or substrate to for instance growing cells, the invention also relates to support devices in general.

The invention will be further described with reference to the following examples and figures which are given by way of illustration and are not intended to limit the invention in any way whatsoever.

FIGURES

FIG. 1. Young's Modulus, the stress at yield ($\sigma_{yield}$) and the maximum tensile strength ($\sigma_{max}$) as a function of the number average molecular weight ($\overline{M}_n$) of poly(TMC).

Figure 2:
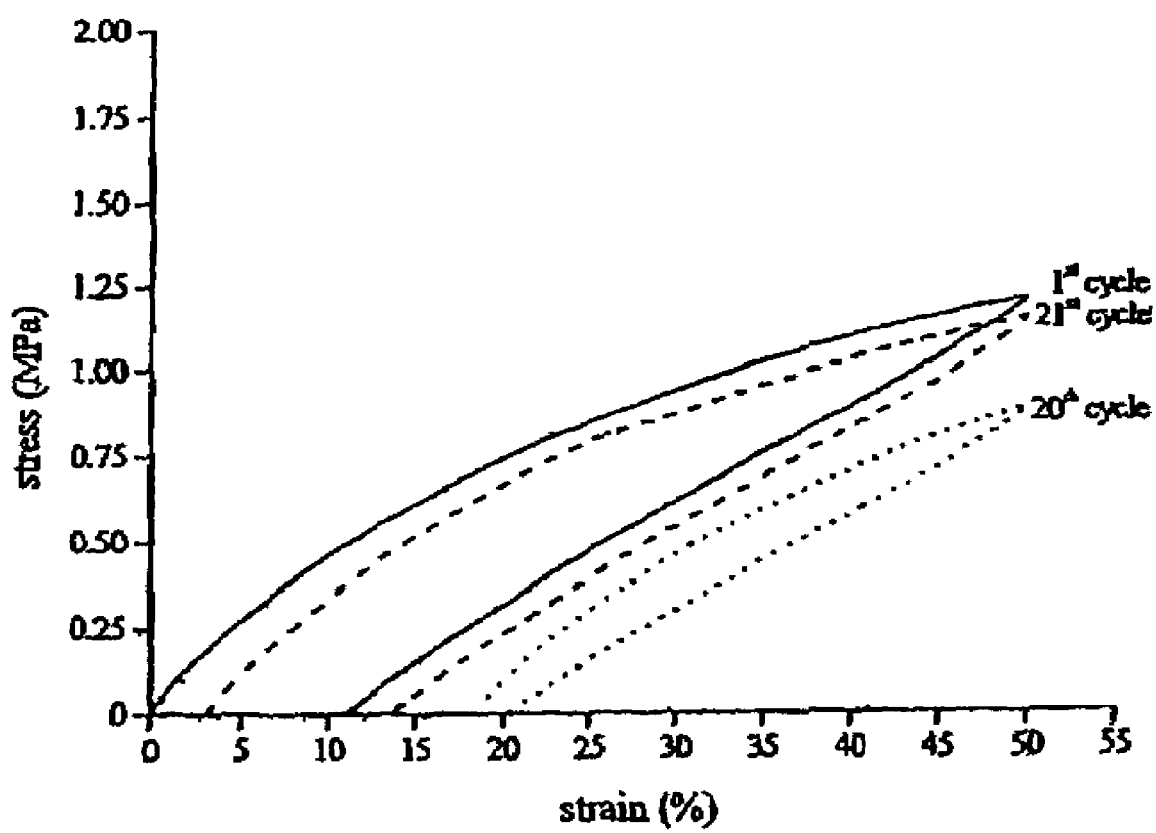

FIG. 2. The cyclic tensile testing of poly(TMC)$_5$ after gamma irradiation at 25 kGy.

EXAMPLES

Example 1

Irradiated Structures of a Homopolymer of TMC (1,3-trimethylene carbonate)(poly(1,3-trimethylene carbonate))

The following example illustrates the preparation and characterization of shaped biodegradable elastomeric structures according to the invention based on a homopolymer of 1,3-trimethylene carbonate (TMC)

Material and Methods

Polymer Synthesis

In an argon atmosphere a quantity of 1,3 trimethylene carbonate (Boehringer Ingelheim Bioproducts Partnership, Germany) is charged in freshly silanized and dried glass ampoules. $2 \times 10^{-4}$ mol stannous octoate per mol monomer was added as solution in sodium dried pentane. The pentane was then removed by means of evacuation. The ampoules were purged three times with dry argon and heat-sealed under vacuum. Different poly(TMC) samples were synthesized (Table I). For the samples 1 and 2, $2 \times 10^{-5}$ mol hexanol was added per mol monomer. In this case the purging step was carried out after cooling the ampoules with liquid nitrogen with the object of preventing evaporation of the hexanol.

By exposing the monomer to air for different periods of time the purity of the monomer can be reduced in a more or less controllable manner. In this way high-molecular poly (TMC) can be obtained with different molecular weights. For the samples 3 to 8 the monomer was exposed to air for a time period of up to 120 min. The heat-sealed ampoules were conditioned in an oil bath preheated to the polymerization temperature and shaken forcefully to obtain a homogeneous mixture of the monomer and the catalyst. Polymerization was carried out for a period of 2 hours (sample 1), of 3 hours (sample 2) or of 3 days at 130° C.±2° C. for the other polymer samples. After the selected reaction time the ampoules were cooled quickly to room temperature and the polymers were discharged. The polymers were purified using dissolution in chloroform (2-5% wt/vol), filtration of the solutions through a sintered glass filter and subsequent precipitation in a tenfold volume of methanol. The polymers were then collected and dried under reduced pressure at room temperature until they had a constant weight.

Polymer Characterization

Polymers were characterized with respect to chemical composition by nuclear magnetic resonance (NMR). 300 MHz $^1$H-NMR (Varian Inova 300 MHz) spectra were recorded using solutions of polymer in CDCl$_3$ (Sigma, USA). Weight average $\overline{M}_w$ and number average $\overline{M}_n$ molecular weights, polydispersity index (PDI) and intrinsic viscosity ([η]) were determined by gel permeation chromatography (GPC) using a Waters Model 510 pump (USA), a HP Ti-Series 1050 autosampler (USA), a Waters Model 410 Differential Refractomer and a Viscotek H502 Viscometer Detector (USA) with Waters Styragel HR5-HR4-HR2-HR1 columns placed in series. Chloroform was used as eluent at a flow rate of 1.5 ml/min. Narrow polystyrene standards were used for calibration. Sample concentrations of approximately 0.5 wt/vol % and injection volumes of 30 µl were used. All determinations were performed at 25° C.

The thermal properties of the purified polymers were evaluated by differential scanning calorimetry (DSC). Samples (5-15 mg) placed in aluminum pans were analyzed with a Perkin Elmer Pyrisl (USA) at a heating rate of 10° C./min. All samples were heated to 40° C. above their melting temperature (when present) or glass transition temperature. The samples were then quenched rapidly (300° C./min) to 40° C. below their glass transition temperature and after 5 min a second scan was recorded. The glass transition temperature ($T_g$) was taken as the midpoint of the heat capacity change. Cyclohexane, indium, gallium and tin were used as standards for temperature calibration.

TABLE 1

Characterization of the TMC homopolymers after purification

| Sample | $\overline{M}_n * 10^{-5}$ | $\overline{M}_w * 10^{-5}$ | PDI | [η] (dl/g) | Tg (° C.) |
|---|---|---|---|---|---|
| Poly(TMC)$_1$ | 0.57 | 0.92 | 1.62 | 1.19 | −19 |
| Poly(TMC)$_2$ | 1.09 | 1.85 | 1.7  | 1.79 | −18 |
| Poly(TMC)$_3$ | 2.72 | 5.38 | 1.98 | 4.51 | −19 |
| Poly(TMC)$_4$ | 3.06 | 5.3  | 1.73 | 4.29 | −17 |
| Poly(TMC)$_5$ | 3.27 | 4.82 | 1.47 | 4.2  | −19 |
| Poly(TMC)$_6$ | 3.33 | 5.83 | 1.75 | 4.52 | −17 |
| Poly(TMC)$_7$ | 3.37 | 5.59 | 1.67 | 4.49 | −17 |
| Poly(TMC)$_8$ | 3.55 | 6.17 | 1.74 | 4.85 | −18 |

The Young's Modulus, the yield stress ($\sigma_{yield}$) and the maximum stress ($\sigma_{max}$) as a function of the number average molecular weight ($\overline{M}_n$) of the poly(TMC) polymers is shown in FIG. 1.

Molding of Polymer Structures

Compression-molding of the purified polymers was carried out using a Fontijne laboratory press THB008 in stainless steel molds with a thickness of 600 µm. The films were compressed at 140° C. and then cooled under pressure to 15° C.

Mechanical Properties

Tensile tests were performed on compression-molded films with dimensions in accordance to ASTM standard D882-91 specifications (100×5×0.6 mm$^3$). The mechanical tests were carried out on a Zwick Z020 universal tensile testing machine (Germany) at room temperature (18-20° C.). Tensile tests were carried out on the tensile testing machine equipped with a 500 N load cell, operated at a crosshead speed of 50 mm/min. The specimen deformation was derived from the grip-to-grip separation, the initial grip-to-grip separation being 50 mm.

Gamma Irradiation

Poly(TMC) samples were placed in bags of poly(ethylene)/poly(amide) under vacuum, under N$_2$, or under air, and sealed. The samples were exposed to 15, 25 and 50 kGy gamma radiation obtained from a $^{60}$Co source (Gammamaster, Ede, The Netherlands).

Equilibrium swelling experiments were carried out in chloroform at room temperature. The samples were swollen for one week in order to achieve equilibrium and the extracted gels were then dried in a vacuum at room temperature for two weeks until they had a constant weight. The gel and sol fractions of the irradiated samples were calculated according to equation 3 and 4, respectively.

$$\text{gel fraction} = m_d/m_i \quad (3)$$

$$\text{sol fraction} = 1 - (m_d/m_i) \quad (4)$$

wherein $m_d$ is the mass of the extracted and dried gels and $m_i$ is the mass of the specimens before swelling and extraction. The degree of swelling (q) was calculated from the ratio of the weight of swollen and extracted samples ($m_s$) and the dried gels ($m_d$) and the specific densities of solvent ($\rho_s$) (1.4832 g/cm3 for chloroform) and poly(TMC) ($\rho$=1.31 g/cm$^3$) using:

$$q = 1 + \rho^*[(m_s/(m_d^* \rho_s)) - (1/\rho_s)] \quad (5)$$

Results

After irradiation structures of poly(TMC) were obtained with a degree of swelling and a gel fraction as shown in table 2.

TABLE 2

Degree of swelling and gel fraction of poly(TMC) films treated with different gamma-radiation doses.

| Irradiation dosage (kGy) | Degree of swelling (%) | Gel fraction (wt %) |
|---|---|---|
| 15 | 355 | 15 |
| 25 | 140 | 33 |
| 40 | 61 | 51 |

Table 3 shows the degree of swelling and the gel fraction of poly(TMC) after gamma irradiation at 25 kGy under vacuum, under nitrogen and under air.

TABLE 3

Degree of swelling and gel fraction of poly(TMC) treated with a 25 kGy gamma radiation dose under vacuum or in a nitrogen or air atmosphere.

| Atmosphere | Degree of swelling (%) | Gel fraction (wt %) |
|---|---|---|
| vacuum | 84 | 54 |
| nitrogen | 83 | 48 |
| air | 107 | 29 |

A significant improvement was observed with respect to the permanent deformation during cyclic deformation up to 50% strain of the irradiated samples. Compared with the untreated samples, the irradiated samples displayed a better recovery 2 hours after 20 successive deformation cycles (the permanent deformation was 4.6% for the untreated samples and 3% for the irradiated samples, see FIG. 2), and a much higher creep resistance (Table 4). The applied stresses of 0.1 MPa, 0.2 MPa, 0.4 MPa and 0.6 MPa in Table 4 correspond to 5%, 10%, 20% and 30% of the yield stress of poly(TMC)$_3$, respectively.

TABLE 4

Creep behaviour of high molecular weight poly(TMC)$_3$ after gamma-irradiation treatment (25 kGy) in the presence or absence of air. (non-extracted films)

| Applied stress (MPa) | Plateau creep rate (s$^{-1}$), vacuum | Plateau creep rate (s$^{-1}$), air | Plateau creep rate (s$^{-1}$) untreated |
|---|---|---|---|
| 0.1 | 0.4 × 10$^{-5}$ | 0.9 × 10$^{-5}$ | 1.9 × 10$^{-5}$ |
| 0.2 | 1.2 × 10$^{-5}$ | 1.9 × 10$^{-5}$ | 2.4 × 10$^{-5}$ |
| 0.4 | 2.7 × 10$^{-5}$ | 8.8 × 10$^{-5}$ | 3.8 × 10$^{-5}$ |
| 0.6 | 6.5 × 10$^{-5}$ | — | 12.5 × 10$^{-5}$ |

Conclusion

Gamma irradiation of poly(TMC) results in simultaneous crosslinking and chain-scissioning. The ratio between the chain-scissioning rate and the crosslinking rate is 0.78 per unit of irradiation dosage. After irradiation of the polymer structure a non-soluble network is formed with the formation of more crosslinkages when the irradiation dosage is increased. The (mechanical) properties of the irradiated polymer structures are greatly improved after irradiation, particularly with respect to the creep resistance.

Example 2

Irradiated Structures of a Copolymer of TMC (1,3-trimethylene carbonate) (TMC and ε-caprolactone copolymer)

The following example illustrates the preparation and characterization of shaped biodegradable elastomeric structures according to the invention based on a copolymer of 1,3-trimethylene carbonate (TMC).

Materials and Methods

Materials

Polymer grade 1,3-trimethylene carbonate (TMC) was obtained from Boehringer Ingelheim, Germany. ε-Caprolactone (CL) (Acros Organics, Belgium) was purified by drying over CaH$_2$ (Acros Organics, Belgium) and distillation under reduced argon pressure. Stannous octoate (SnOct$_2$) (stannous 2-ethylhexanoate) was used as received from Sigma, USA. Solvents (Biosolve, The Netherlands) were of analytical grade.

Polymer Synthesis

Copolymers of TMC and ε-caprolactone, poly(TMC-CL), were synthesized by ring-opening polymerization in evacuated and sealed glass ampoules using SnOct$_2$ as catalyst. All polymerizations were carried out for a period of 3 days at 130° C.±2° C. The obtained polymers were purified by dissolution in chloroform and subsequent precipitation into a ten-fold volume of isopropanol. The precipitated polymers were recovered, washed with fresh isopropanol and dried under reduced pressure at room temperature until constant weight.

Polymer Characterization

Polymers were characterized with respect to chemical composition by nuclear magnetic resonance (NMR). 300 MHz $^1$H-NMR (Varian Inova 300 MHz) spectra were recorded using solutions of polymer in CDCl$_3$ (Sigma, USA). Weight average $\overline{M}_w$ and number average $\overline{M}_n$ molecular weights, polydispersity index (PDI) and intrinsic viscosity ([η]) were determined by gel permeation chromatography (GPC) using a Waters Model 510 pump (USA), a HP Ti-Series 1050 autosampler (USA), a Waters Model 410 Differential Refractometer and a Viscotek H502 Viscometer Detector (USA) with Waters Styragel HR5-HR4-HR2-HR1 columns placed in series. Chloroform was used as eluent at a flow rate of 1.5 ml/min. Narrow polystyrene standards were used for calibration. Sample concentrations of approximately 0.5 wt/vol % and injection volumes of 30 μl were used. All determinations were performed at 25° C.

The thermal properties of the purified polymers were evaluated by differential scanning calorimetry (DSC). Samples (5-15 mg) placed in aluminum pans were analyzed with a Perkin Elmer Pyrisl (USA) at a heating rate of 10° C./min. All samples were heated to 40° C. above their melting temperature (when present) or glass transition temperature. The samples were then quenched rapidly (300° C./min) to 40° C. below their glass transition temperature and after 5 min a second scan was recorded. The glass transition temperature (Tg) was taken as the midpoint of the heat capacity change and the peak melting temperature (Tm) was determined from the melting endotherm. Cyclohexane, indium, gallium and tin were used as standards for temperature calibration.

The molar composition, molecular weights and thermal properties of the prepared copolymers are compiled in Table 1.

stants weight. The gel and the sol fractions of the irradiated samples were calculated according to equation 3 and 4, respectively:

$$\text{gel fraction} = m_d/m_i \quad (3)$$

$$\text{sol fraction} = 1 - m_d/m_i \quad (4)$$

where $m_d$ is the mass of the extracted and dried gels and $m_i$ is the mass of the specimens before swelling and extraction. The degree of swelling (q) was calculated from the ratio of the weight of swollen and extracted samples ($m_s$) and the dried gels ($m_d$) and the specific densities of solvent ($\rho_s$) (1.4832 g/cm$^3$ for chloroform) and poly(TMC-CL) ($\rho$=1.31 g/cm$^3$) using:

$$q = 1 + \rho^*[(m_s/(m_d^*\rho_s)) - (1/\rho_s)] \quad (5)$$

Results

The effect of gamma irradiation at different doses on the solubility of compression molded poly(TMC-CL) copolymers is presented in Table 2.

TABLE 1

Characterization of the prepared TMC and CL copolymers.

| Entry | Polymer | $\overline{M}_w \times 10^{-3}$ | $\overline{M}_n \times 10^{-3}$ | PDI | $[\eta]^a$ (dl/g) | $T_g^b$ (° C.) | $T_m^b$ (° C.) |
|---|---|---|---|---|---|---|---|
| 1 | poly(TMC-CL) (10:90 mol %) | 182 | 98 | 1.9 | 2.5 | — | — |
| 2 | poly(TMC-CL) (11:89 mol %) | 220 | 130 | 1.7 | 3.8 | −64 | 37 |
| 3 | poly(TMC-CL) (10:90 mol %) | 186 | 98 | 1.9 | — | −61 | 48 |

$^a$In CHCl$_3$, at 25° C.
$^b$Second heating scan (DSC).

Polymer Processing

Compression molding of purified polymers was done on a Fontijne laboratory press THB008 (The Netherlands) in 600 μm thick stainless steel molds. The films were melt-pressed at 140°C and subsequently cooled to 15° C. under pressure.

Mechanical Properties

Tensile tests were performed on compression-molded films with dimensions in accordance to ASTM standard D882-91 specifications (100×5×0.6 mm$^3$). The mechanical tests were carried out on a Zwick Z020 universal tensile testing machine (Germany) at room temperature (18-20° C.). Tensile tests were carried out on the tensile testing machine equipped with a 500 N load cell, operated at a crosshead speed of 50 mm/min. The specimen deformation was derived from the grip-to-grip separation, the initial grip-to-grip separation being 50 mm.

Gamma-Irradiation

Samples were placed in poly(ethylene)/poly(amide) bags and sealed after evacuation. The samples were exposed to 15, 25 and 40 kGy gamma-irradiation from a $^{60}$Co source (Gammaster, Ede, The Netherlands). Equilibrium swelling experiments were performed at room temperature using chloroform. The samples were swollen for one week to reach equilibrium and subsequently the extracted gels were dried under vacuum at room temperature for two weeks until con-

TABLE 2

Solubility and swelling behavior of TMC and CL copolymers (entry numbers as in Table 1) irradiated with gamma radiation after compression molding.

| entry | polymer | gamma irradiation dose (kGy) | soluble$^a$ | gel fraction (%) | degree of swelling |
|---|---|---|---|---|---|
| 1 | poly(TMC-CL) (10:90 mol %) | 15 | yes$^b$ | 0 | soluble |
| 1 | poly(TMC-CL) (10:90 mol %) | 25 | no | c | c |
| 1 | poly(TMC-CL) (10:90 mol %) | 40 | no | c | c |
| 2 | poly(TMC-CL) (11:89 mol %) | 50 | no | c | c |
| 3 | poly(TMC-CL) (10:90 mol %) | 50 | no | 42.8 | 55.9 |

$^a$In CHCl$_3$, at 25° C.
$^b\overline{M}_w$ and $\overline{M}_n$ were respectively 263 × 10$^3$ and 77 × 10$^3$ g/mol after irradiation
$^c$Not determined It can be seen that irradiation of the TMC and CL copolymers at irradiation doses higher than 25 kGy results in the formation of an insoluble network. At a low irradiation dose of 15 kGy the copolymer was soluble, although the increase in the ratio of $\overline{M}_w$ to $\overline{M}_n$ indicates the formation of a branched structure.

The effect of gamma irradiation on the tensile properties of poly(TMC-CL) copolymers is presented in Table 3. The table shows that upon 50 kGy gamma irradiation the E-modulus and yield stress values are increased. This indicates that a stiffer and more elastic material has been formed.

TABLE 3

Tensile properties of compression molded TMC and CL copolymers before and after gamma irradiation (entry numbers as in table 1).

| entry | polymer | gamma irradiation dose (kGy) | E (MPa) | yield stress (MPa) | maximal stress (MPa) | Elongation at break (%) |
|---|---|---|---|---|---|---|
| 3 | poly(TMC-CL) (10:90 mol %) | 0 | 215 | 9.5 | 13.7 | >550 |
| 3 | poly(TMC-CL) (10:90 mol %) | 50 | 250 | 12.2 | 12.2 | >550 |

Conclusion

Poly(TMC-CL) copolymers can be crosslinked by gamma irradiation. The formed networks are insoluble in organic solvents and have a high gel content. The (mechanical) properties improve upon gamma irradiation, resulting in stiffer and more elastic materials. Upon irradiation at lower doses, a branched polymeric structure is obtained.

The invention claimed is:

1. Method for providing a shaped biodegradable elastomeric structure, comprising:
    forming at least one of homopolymers and copolymers of 1,3-trimethylene carbonate (TMC) into a desired shape; and
    irradiating said desired shape with actinic radiation in an inert atmosphere for crosslinking,
    wherein the copolymer of 1,3-trimethylene carbonate (TMC) is chosen from the group consisting of 1,3-trimethylene carbonate (TMC) (co)polymers with polyethylene oxide (PEO), polyethylene glycol (PEG) and -caprolactone (CL).

2. Method according to claim 1, wherein the at least one of the homopolymer and copolymer of 1,3-trimethylene carbonate (TMC) includes a number average molecular weight ($M_n$) greater than 10,000.

3. Method according to claim 1, wherein the copolymer of 1,3-trimethylene carbonate (TMC) is chosen from the group consisting of a statistical copolymer, a random copolymer, an alternating copolymer, a block polymer, a diblock copolymer, a triblock copolymer, a multiblock copolymer, a star-shaped block copolymer, and a graft block copolymer.

4. Method according to claim 1, wherein the copolymer of 1,3-trimethylene carbonate (TMC) is poly(1,3,-trimethylene carbonate-co-,-caprolactone)(poly(TMC-CL)).

5. Method according to claim 1, wherein the actinic radiation is chosen from the group consisting of gamma radiation, high-energy UV radiation and electron radiation.

6. Method according to claim 1, wherein the actinic radiation is gamma radiation and the irradiation dosage is 5-100 kGy.

7. Method according to claim 1, wherein the inert atmosphere is obtained by use of a reduced pressure of less than $10^4$ Pa.

8. Method according to claim 1, wherein the inert atmosphere is obtained by use of an inert gas.

9. Method according to claim 1, wherein a creep rate of the provided shaped biodegradable elastomeric structure is less than 10% of the yield stress.

10. Method according to claim 1, wherein a degree of swelling of the provided shaped biodegradable elastomeric structure is less than 400% in chloroform.

11. Method according to claim 1, wherein a gel fraction of the provided shaped biodegradable elastomeric structure is more than 10% by weight.

12. Method according to claim 1, further comprising sterilizing the provided shaped biodegradable elastomeric structure.

13. Shaped biodegradable elastomeric structure obtainable by a method according to claim 1.

14. A method, comprising:
    using a shaped biodegradable elastomeric structure according to claim 13 in or as at least one of an implant, a matrix and a support device.

15. A medical implant, comprising:
    a shaped biodegradable elastomeric structure according to claim 13.

16. Method according to claim 1, wherein the at least one of the homopolymer and copolymer of 1,3-trimethylene carbonate (TMC) includes a number average molecular weight ($M_n$) between 10,000 to 300,000.

17. Method according to claim 1, wherein the at least one of the homopolymer and copolymer of 1,3-trimethylene carbonate (TMC) includes a number average molecular weight ($M_n$) between 50,000 to 200,000.

18. Method according to claim 1, wherein the actinic radiation is gamma radiation and the irradiation dosage is 10-45 kGy.

19. Method according to claim 1, wherein the sterilizing of the provided shaped biodegradable elastomeric structure is done in an autoclave.

20. A matrix, comprising:
    a shaped biodegradable elastomeric structure according to claim 13.

21. A support device, comprising:
    a shaped biodegradable elastomeric structure according to claim 13.

* * * * *